US011255777B2

(12) United States Patent
Chambers

(10) Patent No.: US 11,255,777 B2
(45) Date of Patent: *Feb. 22, 2022

(54) AUTOMATED REMOTE GAS MONITORING AND FLARE CONTROL SYSTEM

(71) Applicant: Daniel W Chambers, San Diego, CA (US)

(72) Inventor: Daniel W Chambers, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/064,142

(22) Filed: Oct. 6, 2020

(65) Prior Publication Data

US 2021/0063304 A1    Mar. 4, 2021

Related U.S. Application Data

(63) Continuation-in-part of application No. 16/429,615, filed on Jun. 3, 2019, now Pat. No. 10,850,314.

(60) Provisional application No. 62/680,329, filed on Jun. 4, 2018.

(51) Int. Cl.
| | |
|---|---|
| *E21B 41/00* | (2006.01) |
| *E21F 7/00* | (2006.01) |
| *F02B 43/00* | (2006.01) |
| *G01N 21/3504* | (2014.01) |
| *G01N 33/24* | (2006.01) |
| *G01N 1/24* | (2006.01) |
| *G01N 33/00* | (2006.01) |

(52) U.S. Cl.
CPC ........... *G01N 21/3504* (2013.01); *G01N 1/24* (2013.01); *G01N 33/0063* (2013.01); *G01N 33/24* (2013.01)

(58) Field of Classification Search
CPC ..... B09B 1/006; E21B 43/00; E21B 41/0092; F23G 7/08; G01N 33/225; G01N 33/24; F02B 43/00
USPC .......................................... 405/129.1–129.95
See application file for complete search history.

(56) References Cited

U.S. PATENT DOCUMENTS

| | | | | |
|---|---|---|---|---|
| 3,779,689 A | * | 12/1973 | Reed .......................... | F23G 7/08 431/89 |
| 3,887,324 A | * | 6/1975 | Reed ........................ | F23N 1/025 431/5 |
| 4,208,224 A | * | 6/1980 | Girrell ...................... | C21D 1/74 148/216 |
| 4,907,964 A | * | 3/1990 | Howarth ................... | F23G 7/08 431/202 |
| 5,842,357 A | * | 12/1998 | Siwajek ................... | C01B 32/50 62/625 |
| 6,033,207 A | * | 3/2000 | Cummings ................ | F02C 3/22 431/11 |

(Continued)

*Primary Examiner* — Edwin J Toledo-Duran
(74) *Attorney, Agent, or Firm* — Olson & Cepuritis, LTD.

(57) ABSTRACT

The present invention comprises a remote gas monitoring system (RGMS) which improves soil-gas monitoring and data management tasks at landfills and other impacted sites while reducing errors in data collection. The remote gas monitoring system incorporates multiple remote gas monitoring sensors and allows for continuous monitoring of landfill soil-gas composition and more efficient and cost-effective operation of a landfill flare system. The invention also comprises a method of controlling the operation of a landfill flare by signaling the flare to begin and cease operation based on predetermined threshold landfill gas concentrations.

8 Claims, 8 Drawing Sheets

(56) References Cited

U.S. PATENT DOCUMENTS

| Patent/Publication | Date | Inventor | Classification |
|---|---|---|---|
| 6,176,224 B1* | 1/2001 | Wu | F02D 19/023 123/527 |
| 6,205,793 B1* | 3/2001 | Schimp | F17C 11/007 62/46.1 |
| 6,393,821 B1* | 5/2002 | Prabhu | F02C 3/22 60/39.465 |
| 6,494,191 B2* | 12/2002 | Bingham | F17C 7/00 123/527 |
| 6,569,236 B1* | 5/2003 | Morimoto | C30B 15/14 117/15 |
| 6,578,559 B2* | 6/2003 | Kilmer | F02M 21/0209 123/527 |
| 6,709,560 B2* | 3/2004 | Andelman | C02F 1/008 204/630 |
| 6,824,224 B1* | 11/2004 | Guadagno | E21B 43/295 299/2 |
| 7,334,391 B2* | 2/2008 | Sako | F02C 9/48 60/39.27 |
| 7,363,883 B2* | 4/2008 | Ito | F02M 21/0278 123/3 |
| 7,591,866 B2* | 9/2009 | Bose | B01D 53/24 55/317 |
| 7,716,063 B2* | 5/2010 | Zimmerman | G06Q 10/04 705/317 |
| 7,875,173 B1* | 1/2011 | Barnes | C02F 1/78 210/167.1 |
| 10,190,392 B1* | 1/2019 | Bachus | B09B 1/006 |
| 2003/0008381 A1* | 1/2003 | Augenstein | A61L 9/00 435/266 |
| 2005/0154669 A1* | 7/2005 | Streetman | G06Q 40/025 705/38 |
| 2007/0068386 A1* | 3/2007 | Mitariten | B01D 53/04 95/116 |
| 2007/0095205 A1* | 5/2007 | Palumbo | C10L 3/102 95/51 |
| 2007/0192221 A1* | 8/2007 | Sandor | G06Q 40/00 705/35 |
| 2007/0225923 A1* | 9/2007 | Tooley | B09B 1/006 702/47 |
| 2007/0250329 A1* | 10/2007 | Richards | G06Q 10/00 705/1.1 |
| 2007/0254196 A1* | 11/2007 | Richards | F01D 15/10 60/39.281 |
| 2007/0286746 A1* | 12/2007 | Thrasher | F04B 5/02 417/404 |
| 2008/0011248 A1* | 1/2008 | Cutlip | F02M 21/0215 123/3 |
| 2008/0015976 A1* | 1/2008 | Sandor | G06Q 40/04 705/37 |
| 2008/0127726 A1* | 6/2008 | Elkins | E21B 47/00 73/152.42 |
| 2008/0183523 A1* | 7/2008 | Dikeman | G06Q 10/06395 705/7.41 |
| 2008/0201255 A1* | 8/2008 | Green | G06Q 40/04 705/37 |
| 2008/0228665 A1* | 9/2008 | Gotthelf | G06Q 10/06375 705/36 R |
| 2008/0275815 A1* | 11/2008 | Musier | G06Q 20/10 705/39 |
| 2009/0020456 A1* | 1/2009 | Tsangaris | C10J 3/523 208/133 |
| 2009/0063231 A1* | 3/2009 | Campo | G06Q 10/06 705/7.12 |
| 2009/0099962 A1* | 4/2009 | Green | G06Q 40/04 705/39 |
| 2009/0125436 A1* | 5/2009 | Palanchian | G06Q 40/06 705/37 |
| 2009/0157534 A1* | 6/2009 | Arsiwala | G06Q 40/12 705/30 |
| 2009/0171975 A1* | 7/2009 | McConnell | G06Q 10/06 |
| 2009/0200854 A1* | 8/2009 | Vinegar | H01F 29/04 299/5 |
| 2009/0265117 A1* | 10/2009 | Castino | G06Q 10/06 702/24 |
| 2009/0271258 A1* | 10/2009 | Quinn | G06Q 30/02 705/14.1 |
| 2009/0287520 A1* | 11/2009 | Zimmerman | G06Q 10/063 705/7.37 |
| 2009/0315388 A1* | 12/2009 | Refsdal | E21B 43/006 299/5 |
| 2009/0319315 A1* | 12/2009 | Branscomb | G06Q 30/06 705/308 |
| 2010/0005021 A1* | 1/2010 | Ezekiel | G06Q 40/04 705/37 |
| 2010/0005958 A1* | 1/2010 | Seki | B01D 53/0476 95/26 |
| 2010/0038082 A1* | 2/2010 | Zubrin | F27D 17/004 166/268 |
| 2010/0038594 A1* | 2/2010 | Bohlig | C22B 1/24 252/373 |
| 2010/0042420 A1* | 2/2010 | Hutchinson | G06Q 10/06 705/1.1 |
| 2010/0049667 A1* | 2/2010 | Margolis | G06Q 40/06 705/36 R |
| 2010/0058771 A1* | 3/2010 | Gil | C01B 3/52 60/780 |
| 2010/0063902 A1* | 3/2010 | Constantz | G06Q 10/087 705/28 |
| 2010/0070358 A1* | 3/2010 | Olson | G06Q 20/105 705/14.17 |
| 2010/0070404 A1* | 3/2010 | McConnell | G06Q 99/00 705/37 |
| 2010/0071602 A1* | 3/2010 | Hernandez | F23G 5/46 110/244 |
| 2010/0076613 A1* | 3/2010 | Imes | G06Q 50/06 700/287 |
| 2010/0077922 A1* | 4/2010 | Constantz | C01F 11/18 95/236 |
| 2010/0089809 A1* | 4/2010 | Bridle | C02F 9/00 210/142 |
| 2010/0106575 A1* | 4/2010 | Bixby | G06Q 30/018 705/14.11 |
| 2011/0132592 A1* | 6/2011 | Apple | E21B 43/006 166/53 |
| 2014/0252099 A1* | 9/2014 | Hatton | F24F 11/30 236/44 A |
| 2016/0245509 A1* | 8/2016 | Karkow | F23N 5/245 |

* cited by examiner

AUTOMATED REMOTE GAS MONITORING AND FLARE CONTROL SYSTEM

CROSS-REFERENCE TO RELATED APPLICATIONS

This application is a continuation-in-part of U.S. Ser. No. 16/429,615 filed on Jun. 3, 2019, which claims priority of Provisional Application Ser. No. 62/680,329, filed on Jun. 4, 2018, both of which are incorporated herein in their entirety.

FIELD OF THE INVENTION

This invention relates to remote gas monitoring systems at landfills. The system includes a network of extraction wells, methane sensors, and a method of optimizing operation of a landfill flare. In particular, the system includes one or more sensors for remotely monitoring soil-gases at landfills.

BACKGROUND OF THE INVENTION

A primary concern of landfills is the presence and movement of landfill gas, a by-product of landfill decomposition containing a complex mix of different gasses created by microorganisms. Landfill gas migration is dependent upon several variables such as subsurface geology, surface and subsurface development, and building structure and foundation characteristics. Landfills located in geologic units containing gravels and sands are susceptible to lateral gas migration. Surface and subsurface development can also be pathways for lateral gas migration.

Federal, State, and local laws require that structures located on or near landfills, disposal sites, and the surrounding area be monitored for landfill gas migration to protect public health and safety from potential explosion hazards associated with combustible gasses. Combustible gasses can include methane, butane, propane, pentane, and other petroleum-based compounds. Methane, a major component of landfill gas, is explosive in concentrations between 5 and 15 percent by volume in ambient air. Landfill gas can migrate through permeable soils surrounding the landfill, and migrate into nearby structures, utilities, and neighborhoods.

In many U.S. states, regulations require that landfill owners take corrective measures when regulatory threshold levels of landfill gasses are exceeded. Typically, regulations focus on methane gas concentration when regulating landfill gasses. To destroy methane and other harmful landfill gas components, many landfill owners burn off landfill gas via a complex subsurface piping system connected to a flare. In an effort to avoid harmful gas concentrations at or above the regulatory threshold level, landfill owners operate the flare system on a timer. The flare turns on and burns landfill gas for a set amount of time and then turns off. This method is not dependent upon the concentration of the target gas in the landfill gas being burned. The flare will operate and burn propane fuel along with any landfill gasses present, regardless of concentration. Carbon dioxide ($CO_2$), carbon monoxide (CO), nitrogen oxide (NOx), and other emissions are by-products of burning propane and landfill gasses.

Landfill sites no longer in use are capped with a non-permeable material to create a closed system. The sites are equipped with extraction wells to collect and dispose of landfill gas. Extraction wells generally include a network of horizontal pipes beneath the surface connected to a series of above ground collection pipes leading to a flare furnace and stack. A plurality of the extraction wells are used to monitor the concentration of landfill gasses in wellhead ambient air and migration of landfill gasses across the site.

Typically, landfill gas and vapor intrusion soil-gas studies are conducted monthly using hand-held monitoring and sampling equipment to collect soil-gas data from the wells. The sampling equipment includes sensors calibrated to a target gas, a known source and concentration of a combustible gas, such as methane. A field technician removes the cap from the well or sampling port on the well and inserts a tube from a soil-gas analyzer, such as a Landtech® GEM5000 gas meter or similar, to analyze the gasses collected in the well. The data from the gas analyzer is stored in the meter for later download or written down on a field data sheet. The field data is transferred or inputted into a computer database manually for analysis and reporting. This method is labor intensive, costly, and subject to human error and data manipulation. In the aforementioned scenario, there are multiple areas where data collection errors can occur. These include: misidentification of the data point, improper meter calibration, data recorded on field data sheets improperly, improper measuring duration, meter failure, and data loss.

Currently, landfill flares and vapor extraction systems (VES) operate via a timing system, or continuously 24 hours a day at impacted sites. In the case of most landfills, flares operate on a timer for a fixed number of hours daily. The flare systems run daily regardless of actual concentrations of landfill gasses within the soil, extraction wells, or system piping. In the case of most VES systems, the VES operates 24 hours a day.

Operation of a flare system on a timer is inefficient, unnecessarily costly, and hazardous to the environment. The flare may operate when no environmental hazard exists, needlessly burning propane which is costly and releases harmful by-products into the atmosphere. Additionally, the flare system may not be turned on when a dangerous condition does exist, thereby allowing levels of landfill gasses exceeding the minimum threshold to go unmitigated.

Remote monitoring of landfill gasses using the type of sensors that is part of the system disclosed herein allows for more efficient, cost-effective, and accurate monitoring of landfill gas composition, concentration, and migration. Controlling operation of the landfill flare system based on measured landfill gas concentration, or concentration of a target gas, increases efficiency and provides cost savings, as well as reduces emission of propane by-products and the risk of a delay in mitigating elevated landfill gas concentrations.

SUMMARY OF THE INVENTION

The present invention provides for remote monitoring of landfill gasses with more accurate, continuous monitoring, increased efficiency, a reduced risk of error, and greater benefit to the environment. Each wellhead is fitted with a sensor capable of transmitting soil-gas concentration measured by the sensor, typically of a particular target gas selected to be monitored. The type of sensor used is dependent upon the target gas being monitored. The present invention addresses several of the areas where data errors can occur, reduces labor costs, reduces operating costs, reduces unnecessary emission of propane by-products, and can immediately address landfill gas concentrations exceeding a predetermined threshold level. Further, the remote gas monitoring system of the present invention can provide an immediate alert in the event of system failure or a leak, or in the event an unsafe gas concentration detected requiring immediate attention.

Under current methodology, data is collected under a condition of variables that allow for potential error and data loss. These variables include calibration anomalies of the instruments used for gas readings, a variety of different instruments from multiple manufacturers that could vary data, human error in recording data, human error in calibrating equipment, and error in uploading data from field data sheets to computer for data management and analysis. Currently, the only way to know if data errors occur is to monitor the landfill site by hand on a periodic basis as required (weekly, monthly, quarterly) and compare the most recent data to historical data. If a data point shows a change in readings the field scientist must determine if there was an error in monitoring protocols, an error in calibrating the meter, a failure in the meter, or another variable that may have caused the change in data for that location (increase/decrease in soil-gas concentration). Upon installation of a Remote Gas Monitoring System (RGMS) of the present invention, the risks outlined above for errors in data collection would be greatly reduced or eliminated at landfill sites. Remote monitoring also reduces or eliminates the need for technicians to manually sample each well, a labor intensive and costly process.

Under the current data collection protocols, there is no immediate access to data from the field. There is no real-time data sourcing, unless a field technician calls in the data to another project member via cell phone. Under the current monitoring protocols, there is no immediate review of anomalous data. All data is collected in the field and then reviewed for consistencies with historical data at a later time. With an RGMS in place, anomalous data can be immediately identified. Because the opportunity to err in sampling or monitoring protocols is minimized or eliminated with RUMS sensors, the ability to identify the possible data error is immediate, and anomalies can be postulated to sensor failure, data upload failure, breach in probe/piping hardware, or in fact, changes in soil-gas concentrations.

Currently, landfill flare systems are monitored for system integrity visually and/or manually during the periodic landfill gas monitoring intervals. Flare systems have a system warning for non-operation, usually a modem that dials a number and alerts the consultant of a system failure via a pre-recorded alert. The alert does not inform the recipient of the cause or location of the system failure. A technician must respond to the failure notification by going to the site and determining the cause and location of the failure, then correcting the failure condition and re-starting the flare. With the installation of an RGMS, any flare system failures can be identified and isolated within the monitoring grid of the RGMS. With the knowledge of the type and location of failure already known, the time it takes to mitigate the system problem and return the system to an operational state is greatly reduced.

Equipping wellheads with sensors capable of remotely transmitting measured gas concentrations allows for continuous monitoring of gas concentrations. The particular remote gas monitoring sensor disclosed herein accurately and reliably collects soil-gas data for soil-gas below the surface or emitting from the soil surface. The data is immediately transferred to a database for storage, reporting and data analysis.

Once the RGMS is installed, the data stream may be actively and accurately monitored from a remote location and any anomalies quickly identified and rectified either remotely or on site. The system can also be programmed to issue an alert in the event of a system failure or leak in the system. The system can also be programmed to issue an alert if gas concentrations at one or more wellheads exceed a predetermined limit and the area surrounding the wellhead requires immediate attention or remediation.

Continuous monitoring of landfill gas can utilize combustible gas sensors, direct digital control, programmable logic control, and data acquisition systems to track the presence and concentration of a target gas from landfill gas over time and provide the necessary data to document gas levels in structures that may pose a threat to public health and safety. Continuous monitoring can also provide data to a facility owner which can assist in taking corrective measures to mitigate gas migration hazards.

Continuous monitoring of landfill gas concentrations and direct communication with flares and remediation systems also allows for optimization of the operation of landfill flares and soil vapor extraction systems. With the installation of an RGMS, flares and soil vapor extraction systems can be automated to run only when target gas concentrations reach a threshold level and cease running when levels drop. An upper threshold limit can be established to start the flare at a landfill site at any time in the 24-hour cycle. The flare then runs until a lower threshold limit is met, signalling the flare to shut down. By doing so, the amount of fuel and electricity consumed to run the flare is potentially reduced. Additionally, thermal and vapor effluent from the flare stack may also be reduced. As a result of flare run times potentially being reduced, the amount of time and cost spent maintaining the flare system may also be reduced.

For example, methane gas is explosive when the total air gas concentration is at or above about 5% by volume in ambient air. A preferred embodiment of an RGMS installation for monitoring methane concentration includes a site with a plurality of wellheads distributed throughout the site, a portion of which are fitted with remote wellhead sensors. Preferably, a site with 75 wellheads would have approximately 50-75% of the wellheads fitted with remote wellhead sensors. The remote wellhead sensors of the present invention continuously monitor wellhead ambient air for presence and concentration of methane.

The RGMS can be programmed such that when a predetermined amount of wellhead sensors, for example, any three or more wellhead sensors, or about 5% of the wellhead sensors, detect methane concentration at or above a predetermined upper threshold concentration by volume in wellhead ambient air, the controller signals the flare system to turn on. Switches controlled by a gas concentration detector are known in the art. When the flare system turns on, a blower starts blowing and creates a vacuum, a stream of air is forced into the furnace, a stream of propane mixes with the stream of air, and a spark lights the furnace. The furnace burns until a predetermined optimum temperature is reached, for methane this is preferably a minimum of 1200° F. and more preferably 1500° F. When the predetermined temperature is reached, a landfill gas feed valve opens and landfill gas from the extraction wells flows into the system for combustion. When a predetermined number of wellheads sensors, for example, no more than two wellhead sensors, or about 3% of the wellhead sensors, detect methane concentration at or above a predetermined lower threshold concentration by volume in ambient air, the controller signals the flare system to close the landfill gas feed valve and the flare furnace to shut off.

The same principles behind the automated flare system can be applied to vapor extraction systems (VES) at sites other than landfills, with the coincidental advantages seen with automating the systems and reducing the run times of and costs associated with those systems.

DETAILED DESCRIPTION OF THE INVENTION

The RGMS includes a landfill gas monitoring system and a landfill flare control system. The monitoring system relies on extraction wells equipped with wellhead sensors to monitor the landfill gas concentration throughout the site. Monitoring a plurality of wells spaced throughout the site permits monitoring both the site as a whole and specific areas in the event that a particular area needs localized remediation. Continuous real-time remote monitoring of the landfill gas concentration at the extraction wells alerts the landowner of areas that require immediate attention or localized remediation and of potential violation of environmental regulations restricting landfill gas concentrations. Continuous, real-time remote monitoring of the landfill gas concentration at the extraction wells also facilitates optimization of operation of the flare system.

The RGMS automated flare control system utilizes landfill gas concentration data from the wellhead sensors to signal the flare system to start and stop the flare furnace. Data from the landfill gas monitoring system is received and interpreted by a Main Controller. The Main Controller receives the input data through the "Input" port and interprets the data. The Main Controller can be set to send an "alarm" signal from the "Relay Port" whenever certain concentration thresholds are met. The Main Controller thresholds can be set to any gas concentrations desired, dependent upon the detection capabilities of the wellhead sensors in place on the extraction wells. An upper threshold level can be set for signaling the flare system to start and a tower threshold level can be set to signal the flare system to stop. There are multiple "Input" and "Relay" ports on the Main Controller.

System startup occurs when the power supply, preferably a standard 12-volt battery with solar recharge, is connected to the monitoring system Main Controller. When the power supply is connected, the internal clock begins running, and the connected accessories are self-tested for communication and function. Once the internal clock is set (date and time) the system is activated, then automated monitoring is set and begins monitoring.

Remote Monitoring Gas Sensor

Figure 1:
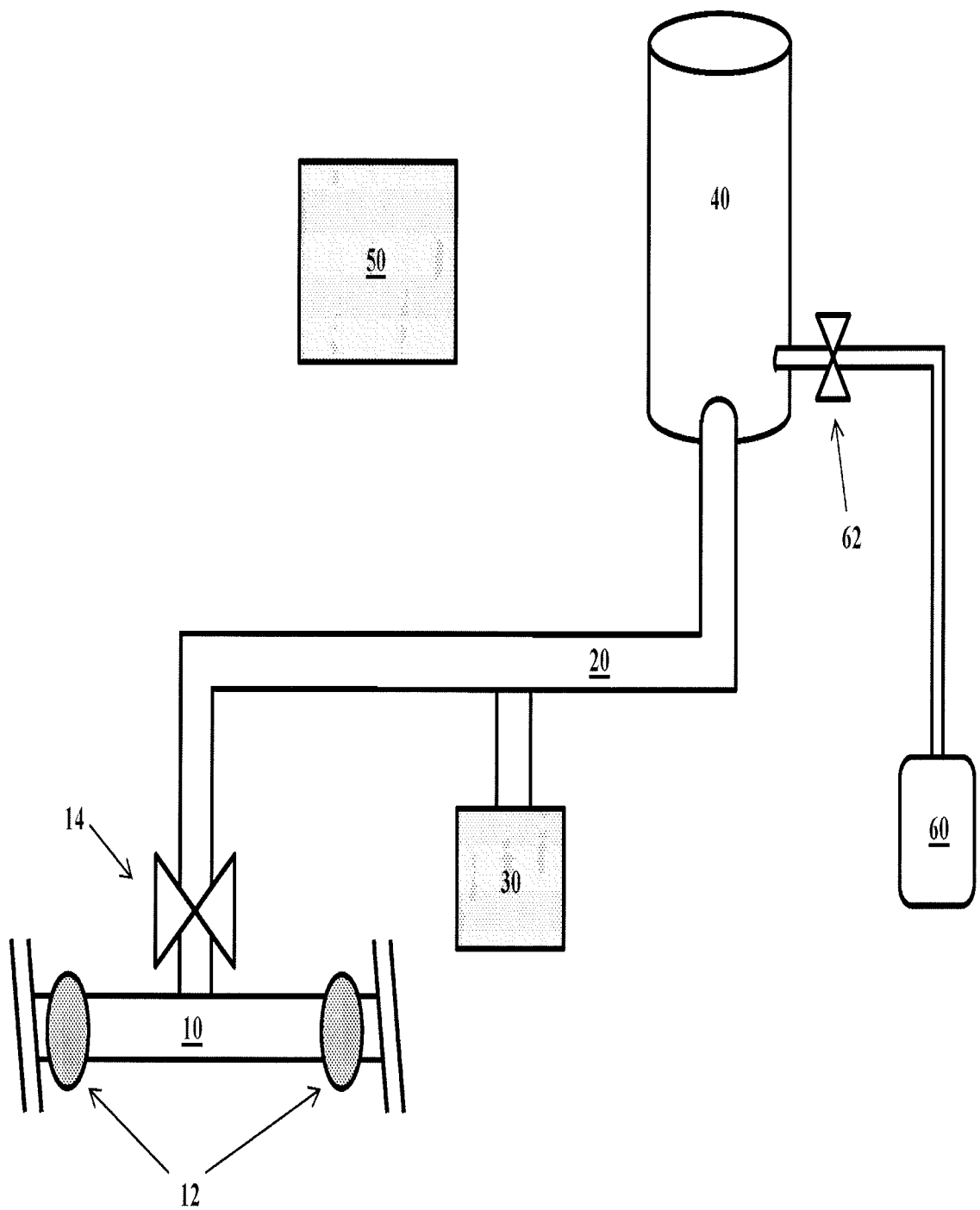
FIG. 1 shows a schematic of the Remote Gas Monitoring System.
Figure 1A:
FIG. 1A shows a front view of a weather-proof case for housing a remote gas monitoring sensor.
Figure 1B:
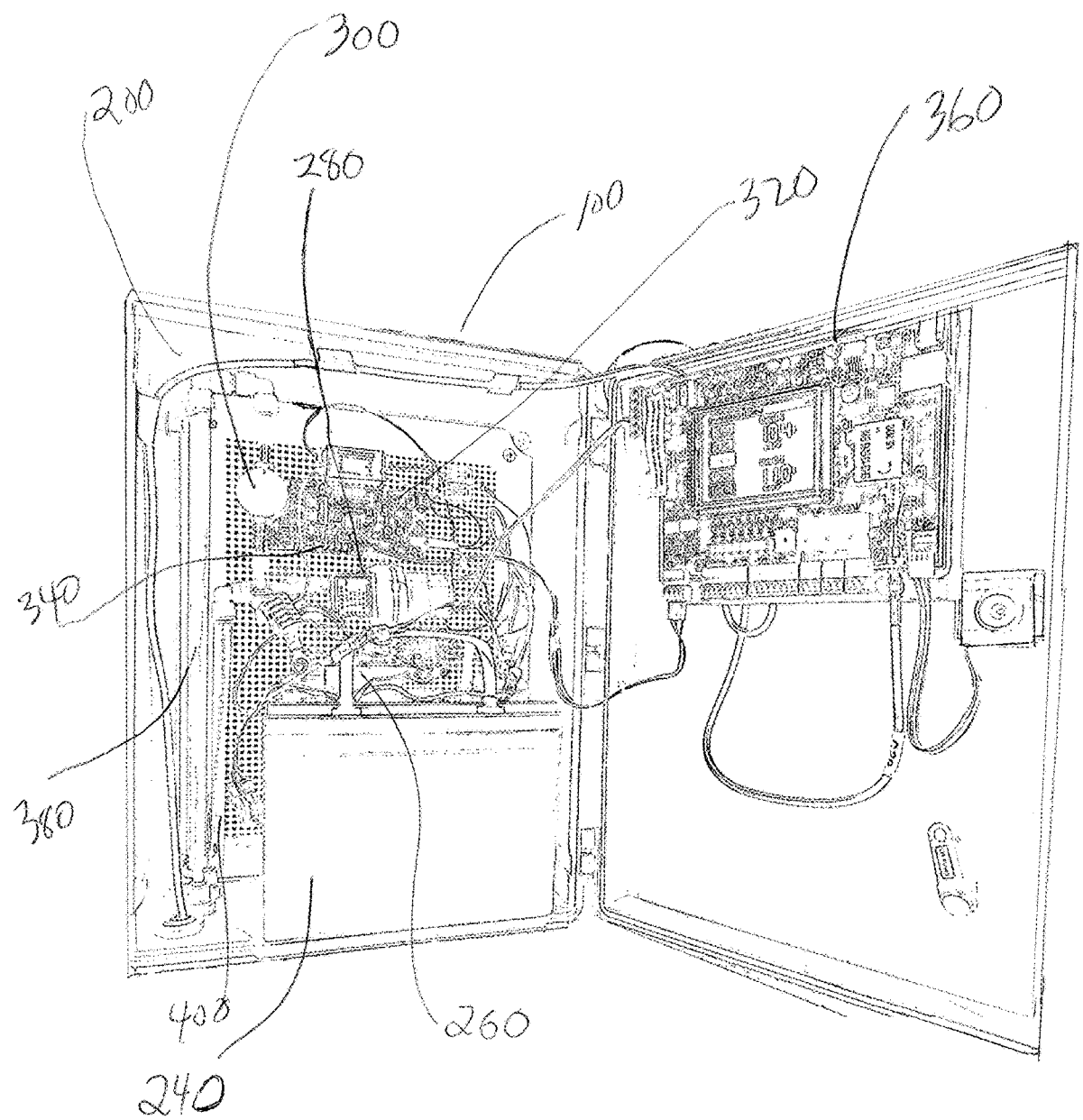
FIG. 1B shows a front view of a remote gas monitoring sensor housed within the weather-proof case of FIG. 1A.

A preferred embodiment of the remote gas monitoring sensor used in the RGMS is shown in FIGS. 1A and 1B. FIG. 1A shows a weather-proof case 100 for housing the remote sensor. Water-proof case 100 is preferably made of polycarbonate materials that is NEMA rated for electrical devices. Extending from water-proof case 100 is an antenna 120 for transmitting data from the remote sensor. All exterior-to-interior passages are sealed bulkhead or similar pass-throughs designed to keep insects and the elements outside of the device interior.

FIG. 1B shows the sensor system 200 which is housed in weather-proof case 100. The sensor system includes a power source 240, a timing system 260, a vacuum pump 280 and gas chamber 300, an infrared dual-gas sensor 320 and sensor board 340, and a data acquisition and telecommunications system 360.

In this embodiment, the power source 240 is a 12-volt battery preferably backed up and recharged by a solar panel. The battery provides continuous power to the data acquisition and telecommunications system 360 and timing system 260. The timing system 260 is used to power the sensor board 340 and the vacuum pump 280 at periodic intervals. The purpose of interval measuring is to reduce wear on the device components and prolong the life of vacuum pump 280 and sensor 320. Timing can be set to run continuously for real-time data where warranted.

Gas chamber 300, preferably made from polycarbonate materials, is affixed to vacuum pump 280 and gas sensor 320 to capture and measure the gasses of concern. Vacuum pump 280 is used to draw gas vapors into gas chamber 300 under a vacuum from a surface or subsurface gaseous point. Vacuum pump 280 ensures that compounds of concern are accurately drawn into gas chamber 300 for measurement by dual-gas sensor 320. Non-dispersing-infrared (NDIR) dual gas sensor 320 is attached to sensor board 340 and is housed in gas chamber 300 to measure the concentration of two gasses. Sensor 320 automatically adjusts for temperature and barometric pressure. Data acquisition and telecommunications system 360 receives the measurement data from sensor board 340 and transmits the data to a database system via a cellular communications network.

When power source 240 is activated in sensor system 200 of FIG. 1B, timing system 260 begins and closes the electrical circuit to sensor board 340 and vacuum pump 280. Simultaneously, power is sent to telecommunications system 360 for receiving and transmitting data. The power supply to the telecommunications board is uninterrupted. When power is applied to vacuum pump 280 and sensor board 340, vapors are drawn into gas chamber 300 through inlet 380 under vacuum from pump 280. While vapors pass through gas chamber 300, dual-gas sensor 320 measures the concentration of target gases and transmits the data to sensor board 340. Sensor board 340 transmits the concentration data to data telecommunication system 360 which then transmits the data to the web-based database via cellular signal. The measured gasses are then vacuumed out of gas chamber 300 through pump 280 and returned to the atmosphere via filtered outlet port 400.

When timing system 260 opens the electrical circuit, vacuum pump 280 and the sensor board 340 are deactivated and enter a resting state. During the resting state gasses are passed through the gas chamber 300 and no measurements are taken. The data telecommunications system 360 remains active.

Timing system 260 is highly variable and can be programmed to measure gases continuously or periodically. Measurements can be read from once a minute, to one time a day. Where conditions warrant, measurements can be set up to take a reading once a week. The frequency of measuring gases will be dependent on the type of gas or gasses measured, the potential concentration of the gasses measured, the required or requested measurement interval requested by the customer or the regulatory agency overseeing the property, or a combination of those factors.

Methane Monitoring

Methane gas poses serious health concerns and is the primary component of landfill gas. The discussion below focuses on monitoring methane gas concentration in landfill gas; however, various sensors can be used to monitor other chemicals or compounds in the system described or within the scope and spirit of the present invention.

The sequence of events that comprises a test cycle for methane monitoring is as follows:
1. $CH_4$ sensor system is actuated for warm-up and self-testing. Flow is established in $CH_4$ sensors.
2. The cellular signal is established for cloud computing by Main Controller.
3. Data is collected and uploaded to data center/software provider.

The methane gas monitoring system is a combination of a plurality of wellhead sensors for detecting methane, a sensor data processor, and a main controller. Preferably, the methane sensors (Direct Connect series sensor model 61-1006RK-CH4 available from RKI Instruments Inc., Union City, Calif.) on the extraction wells are connected directly to the piping of the extraction system. The sensor is plumbed with a tube that transfers gas from the extraction pipe to the sensor body. Wellhead ambient air is analyzed for presence and concentration of methane in the landfill gas and the data is sent to the sensor data processor (Beacon 110 sensor available from RKI Instruments Inc., Union City, Calif.). The data processor takes the data and converts it to be read by the system Main Controller (Mission Communications MyDro-150 available from Mission Communications, LLC, Norcross, Ga.). The Main Controller processes and stores the data and transmits it to the cloud for storage and processing via a built-in cellular signal module. Wellhead ambient air is monitored continuously for presence and concentration of methane in real time 24-hours a day for purposes of activating any alarms and response cycles, if needed. The data from the remote system is uploaded to the internet (Cloud Computing) hourly for storage and retrieval as needed. A person having ordinary skill in the art will appreciate that sensors from other suppliers can be used in the methane monitoring system.

Flare System Optimization

The Flare System at a landfill is comprised of a control panel, a "blower" to generate a vacuum from the extraction wells, and a flare furnace for burning off methane gas and associated landfill gases. Flare System operation is optimized by Main Controller inputs to the Flare System Control Panel. The Flare System at a landfill is designed to destroy methane gas through thereto-oxidation, or "burning." Current flare systems run on a timer with set "start" and "stop" time settings. Current flare systems run for a set number of hours per day regardless of methane or landfill gas concentrations. Some flare systems maintain proper temperature with the use of propane gas to supplement the fuel flow when methane and landfill gas concentrations fall below a threshold level to provide enough fuel for the furnace. Other flare systems shut down when methane and landfill gas concentrations decrease and the proper temperature is lost. Both timer-based systems are inefficient and consume excess fuel and electricity when methane and landfill gas concentrations fluctuate. Furthermore, running flare systems supplemented with propane gas discharges excess heat, CO, and $CO_2$ into the atmosphere. These excess effluents contribute to air pollution. Automated flare systems work in parallel with remote gas monitoring systems to improve methane and other landfill gas destruction, lower costs, and reduce excess effluents.

A schematic of a preferred RGMS is depicted in FIG. 1. As shown in FIG. 1, landfill pipes 10 are fitted with wellhead sensors 12. Wellhead sensors continuously monitor soil-gas concentration. The data measured by wellheads sensors 12 is remotely transmitted to controller 50. If at least about 5% of the sensors detect a target landfill gas concentration by volume in ambient air above an upper threshold level, then controller 50 signals blower 30 to turn on. Blower 30 creates a vacuum forcing a stream of air into piping 20. Tank 60 contains the pilot gas supply, typically propane. Valve 62 opens releasing propane from tank 60 which mixes with the air in pipe 20. The air-propane mixture is forced into flare furnace 40. A spark-ignited pilot ignites the air-propane mixture and flare furnace 40 begins burning. When the temperature in flare furnace 40 reaches a predetermined minimum temperature, landfill gas feed valve 14 opens allowing the landfill gas to flow into inlet piping 20 and then into flare furnace 40 to be burned. When no more than about 3% of sensors 12 detect a target landfill gas concentration by volume in ambient air above a lower threshold level, landfill gas feed valve 14 closes and controller 50 signals flare furnace 40 to cease burning.

Figure 2:
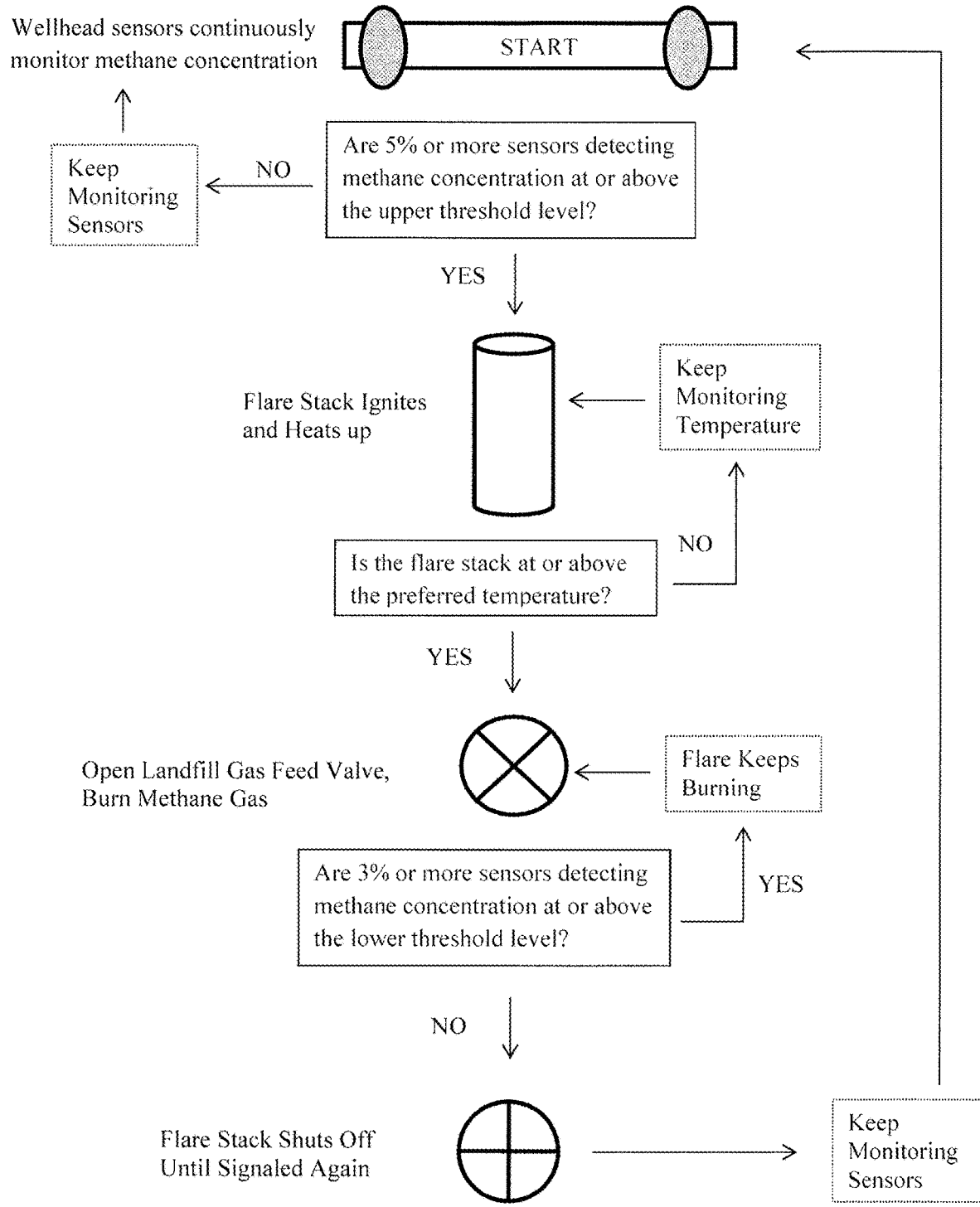
FIG. 2 shows a flow diagram of the operation of the Remote Gas Monitoring System.

A flow diagram of the steps in a preferred RGMS operation for methane destruction is shown in FIG. 2. The wellhead sensors continuously monitor the methane concentration in the wellhead ambient air. If about 5% or more of the sensors detect a methane concentration by volume in wellhead ambient air at or above a predetermined upper threshold level, then the controller signals the flare furnace to ignite. Once the flare furnace reaches a predetermined temperature the landfill gas feed valve opens to allow the landfill gas to enter into the flare furnace and burn. For methane destruction, a minimum temperature of about 1200° F., preferably about 1500° F., is recommended. The flare furnace continues to burn the landfill gas containing methane until no more than about 3% of the sensors, detect a methane concentration by volume in wellhead ambient air above a predetermined lower threshold level. Once this condition is reached, the controller signals the landfill gas feed valve to close and the flare furnace to shut down until signaled again.

Because the methane gas monitoring system monitors methane concentration 24 hours a day in real time, the flare can be run at any time for optimum efficiency and reduction in effluents and costs. Each extraction well is equipped with a valve which can connect the extraction well to the piping system or can seal an extraction well off from the piping system. In the event that a particular area is producing methane gas at levels exceeding levels allowed by current regulations but the overall concentration in the system is not above the threshold level to signal the flare to start, extraction well valves can be opened or closed to connect specific extraction wells to the flare system and the flare can be manually started. This allows for localized remediation of specific areas where methane gas exceeds allowable limits.

Figure 3:
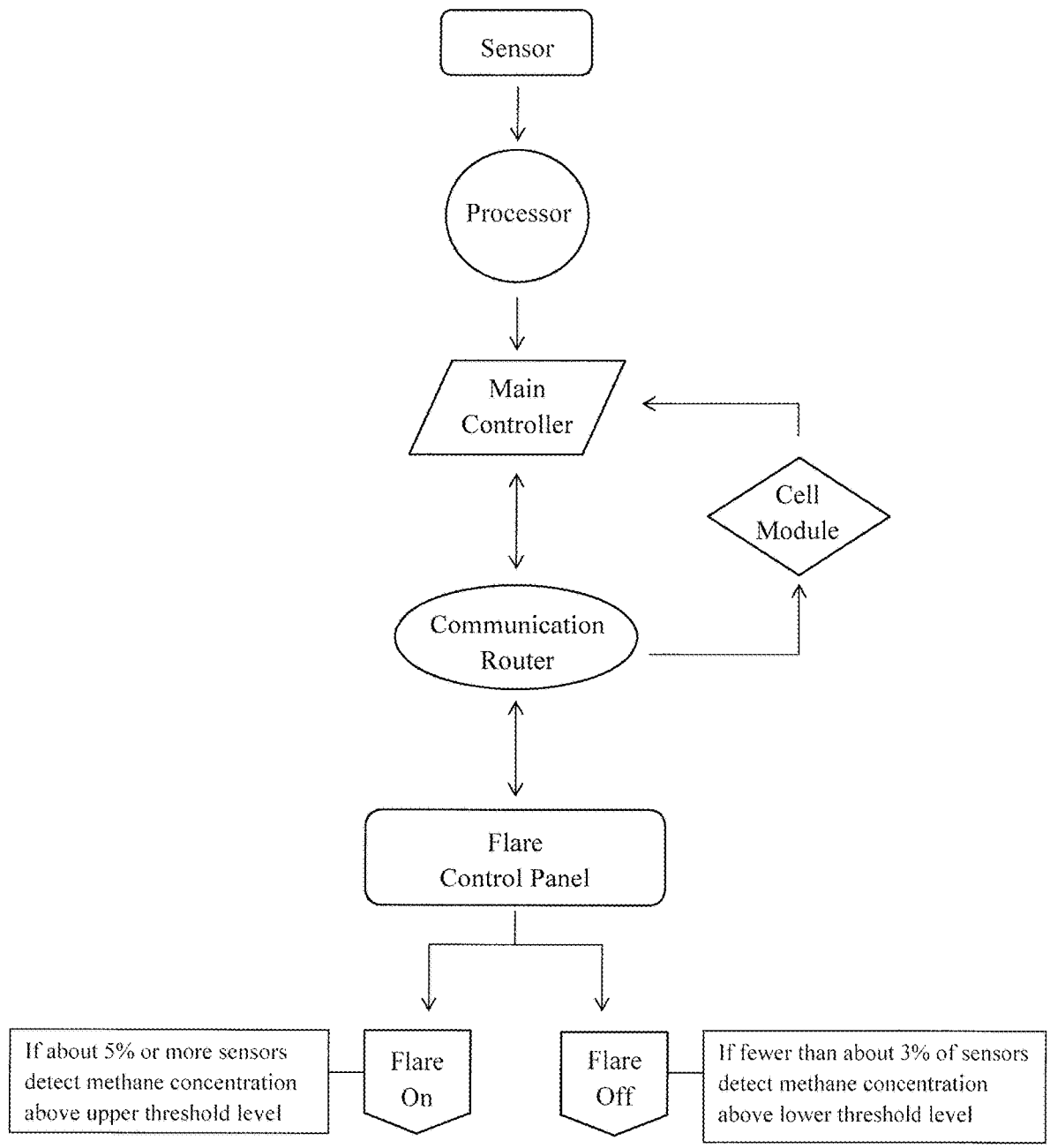
FIG. 3 shows a flow diagram of the system communications.

The Main Controller is connected to the internet 24 hours a day via a built-in cellular signal module. Communication with the Main Controller from a desk top computer, portable computer, "smart phone", tablet, or handheld device can happen at any time as long as an internet connection is established with the computer or hand-held device. The Main Controller on the landfill RGMS is connected to and communicates with the internet 24 hours a day. The communication flow diagram of a typical RGMS for methane destruction is depicted in FIG. 3. As shown in FIG. 3, the methane sensors transmit data to a processor, the processor sends the information to the Main Controller, and the Main Controller sends the information on to the Communication Router. The Communication Router communicates with both the Flare Control Panel, which controls when the flare turns on and off, and with the Cell Module, which reports back to the Main Controller to signal an alarm if a problem is detected.

If there are any desired changes to the monitoring system, data reporting system, or the flare control alarm system, changes can be made remotely with a computer or handheld device. The owner or operator of the RGMS can simply log on to the site database/control system with communication software and make changes to the monitoring and flare control systems 24 hours a day. There is no need to go to the field to make control system changes.

If the system owner wants immediate real-time data, any authorized person can log on to the site database and collect real-time measurements and readings in one-minute parses of data any time of day or night. The remote monitoring system is active 24 hours a day.

Methane Sensor Operating System

A current RGMS in place in Los Angeles, Calif. uses an RKI Direct Connect series sensor model 61-1006RK-CH4 available from RKI Instruments, Union City, Calif. (https://www.rkiinstruments.com/product/direct-connect/). Other sensors are available for use in an RGMS or similar system.

Another sensor for use in this type of system is an infrared (IR) methane sensor, model IR15TT-R Gas Sensor, available from SGX Sensortech, (https://sgx.cdistore.com/ProductDetail/IR15TTR-SGX-Sensortech/362896/) housed in a stand-alone solar powered remote sensor unit. The IR15TT-R sensor is connected to a Mission Communications Main Controller. The Mission Communication Main Controller controls the IR15TT-R sensor and a mini-vacuum pump that transports the landfill gases to the IR15TT-R sensor for analysis. The IR15STT-R sensor sends the detected gas data back to the Mission Communications Controller for data transfer to the cloud, and to an on-board storage data card (Mini-SD card).

Example 1

Remote Monitoring Pilot Study

A small-scale pilot study of the RGMS was conducted at the Chandlers Recycling Ascon Landfill in Wilmington, Calif. The preliminary study focused on using wellhead mounted methane sensors capable of remotely transmitting soil-gas data. Two wellheads located at identified "hot spots", locations of interest for high methane concentration, were equipped with wellhead methane sensors capable of remotely transmitting soil-gas data. This study allowed for continuous monitoring of the landfill resulting in more accurate data and better tracking of methane migration.

Figure 4:
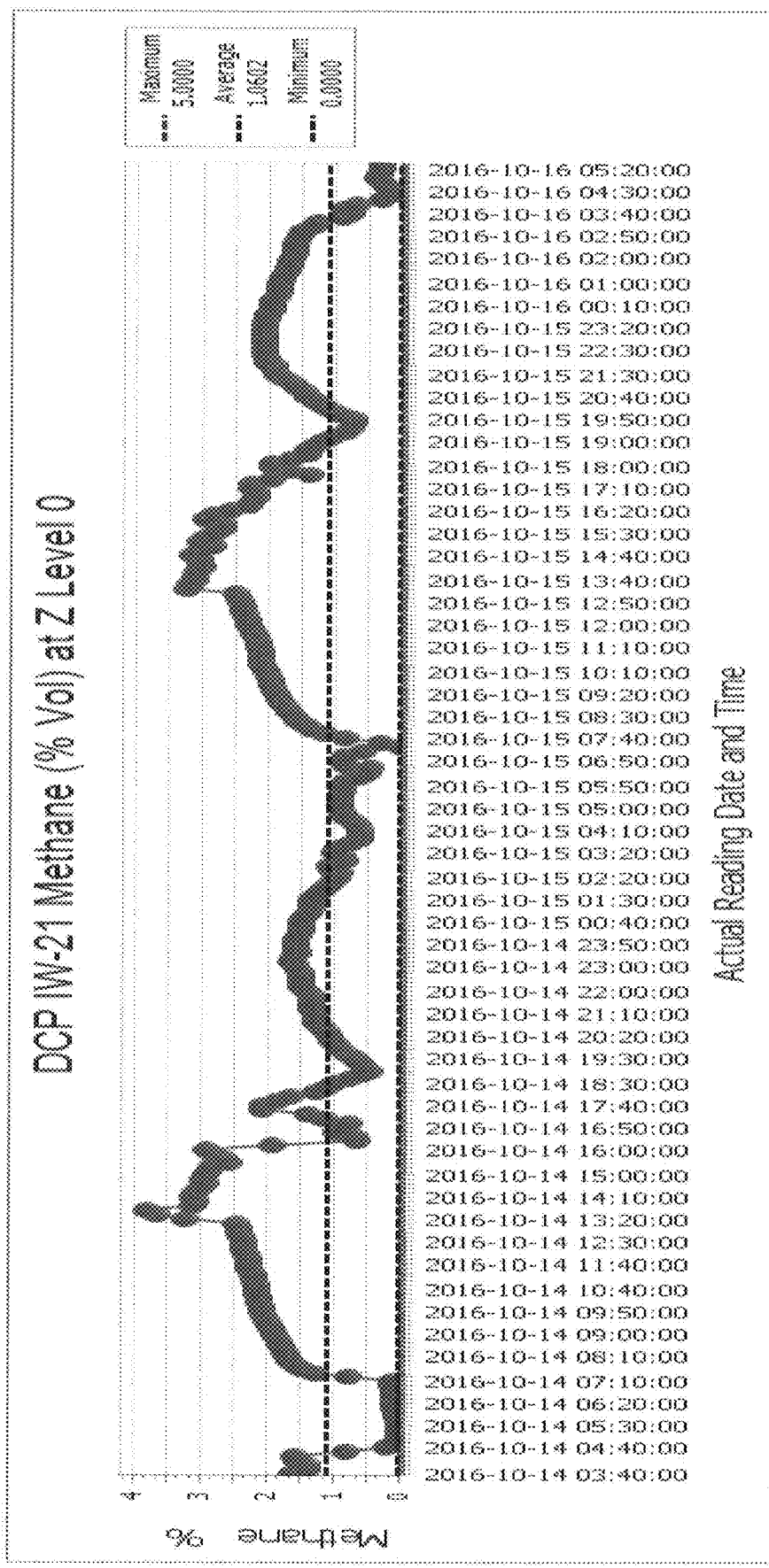
FIG. 4 shows methane concentration measurement at select time points during a pilot test at the Chandlers Recycling Ascon Landfill in Wilmington, Calif. Data was recorded from 14:20 on Oct. 14, 2016 to 16:20 on Oct. 14, 2016.

The wellhead methane sensors monitored methane concentration over time. Select data from the pilot study as recorded on Oct. 14, 2016 is shown in Table 1 and FIGS. 4 and 5. As reported in Table 1, methane concentration data was transmitted from the wellhead sensors every 10 minutes. FIG. 4 shows a graph of methane concentration (% vol.) measured at wellhead IW-21 from Oct. 14, 2016 to Oct. 16, 2016. As reported, the methane concentration fluctuated over time. In this particular test, the flare was operated by a timer. As the data shows, there were few instances where the methane concentration was above 3% at wellhead IW-21 and none where the methane concentration was above 3% at IW-17 Thus, the flare was likely burning when it did not need to be and was unnecessarily burning propane and producing propane by-products when there was not a harmful methane concentration.

Figure 5:
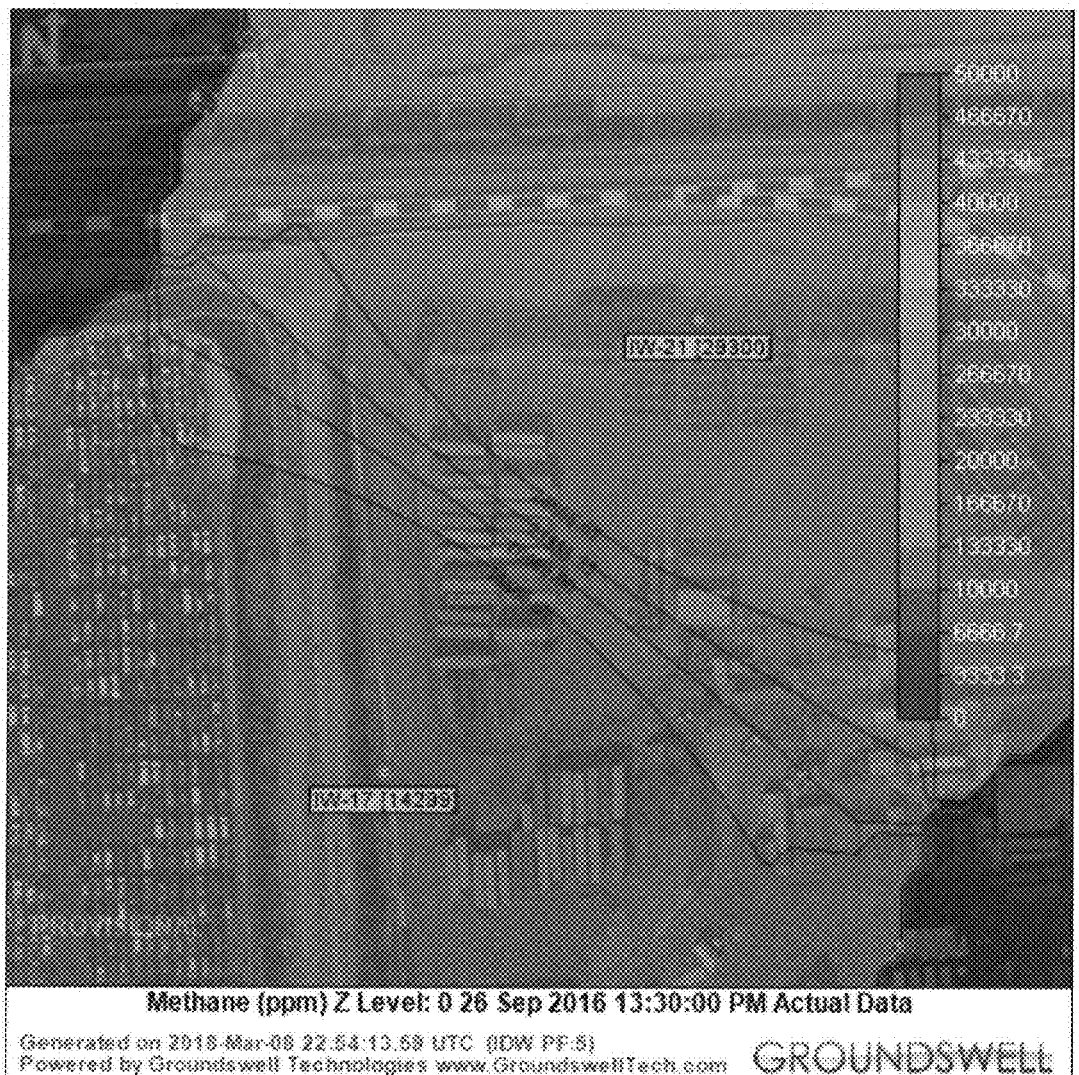
FIG. 5 is a methane concentration overlay showing methane concentration over the Chandlers Recycling Ascon Landfill in Wilmington, Calif. during a pilot test.

FIG. 5 shows the methane gas concentration overlaid over a map of the area. FIG. 5 demonstrates that the methane concentration is not consistent across the test area. The results of the pilot study highlight the need for continuous monitoring of multiple monitoring sites and the potential benefit derived from controlling the landfill flare based on methane concentration rather than on a timer or continuous burning. An RGMS would prevent landfill flare from operating when there is not a methane concentration over an upper threshold limit and would also instruct the flare to operate when there is a detectable methane concentration over the threshold limit. Localized monitoring also provides immediate information regarding "hot spots" or areas in need of localized remediation.

TABLE 1

Methane Concentration as measured on Oct. 14, 2016 at select time points.

| Actual Date and Time | IW-17 Barometric | IW-17 Methane % Vol | IW-17 Methane ppm | IW-21 Barometric | IW-21 Methane % Vol | IW-21 Methane ppm |
|---|---|---|---|---|---|---|
| 2016 Oct. 14 16:20:00 | 31.57 | 0.04 | 400 | 31.77 | 0.66 | 6600 |
| 2016 Oct. 14 16:10:00 | 31.58 | 0.02 | 200 | 31.68 | 1.94 | 19400 |
| 2016 Oct. 14 16:00:00 | 31.61 | 0.05 | 500 | 31.64 | 2.91 | 29100 |
| 2016 Oct. 14 15:50:00 | 31.56 | 0.06 | 600 | 31.72 | 2.81 | 28100 |
| 2016 Oct. 14 15:40:00 | 31.60 | 0.11 | 1100 | 31.72 | 2.65 | 26500 |
| 2016 Oct. 14 15:30:00 | 31.60 | 0.15 | 1500 | 31.54 | 2.58 | 25800 |

TABLE 1-continued

Methane Concentration as measured on Oct. 14, 2016 at select time points.

| Actual Date and Time | IW-17 Barometric | IW-17 Methane % Vol | IW-17 Methane ppm | IW-21 Barometric | IW-21 Methane % Vol | IW-21 Methane ppm |
|---|---|---|---|---|---|---|
| 2016 Oct. 14 15:20:00 | 31.61 | 0.12 | 1200 | 31.58 | 2.8599 | 28599 |
| 2016 Oct. 14 15:10:00 | 31.60 | 0.11 | 1100 | 31.57 | 2.9 | 29000 |
| 2016 Oct. 14 15:00:00 | 31.60 | 0.12 | 1200 | 31.17 | 2.92 | 29200 |
| 2016 Oct. 14 14:50:00 | 31.60 | 0.19 | 1900 | 31.05 | 2.95 | 29500 |
| 2016 Oct. 14 14:40:00 | 31.61 | 0.24 | 2400 | 31.14 | 2.94 | 29400 |
| 2016 Oct. 14 14:30:00 | 31.60 | 0.25 | 2500 | 31.02 | 2.98 | 29800 |
| 2016 Oct. 14 14:20:00 | 31.61 | 0.28 | 2800 | 31.02 | 3.07 | 30700 |

As described herein, several advantages of the RGMS include reduction in labor costs, lower risk of data loss, and fewer data entry errors due to remote monitoring of the sensors, cost savings due to only operating the flare when necessary, and environmental benefits due to only operating the flare when necessary and reduced burning of propane gas. Continuous monitoring with immediate transmittal of data allows for faster response to gas concentrations that exceed allowable limits or safety levels. Continuous monitoring also allows for detection of errors, problems, or leaks in the system sooner. The RGMS also allows for a failsafe which prevents the flare from turning on if the system detects an error.

Example 2

An RGMS system is currently in place at the Chandlers Recycling Ascon Landfill in Wilmington, Calif. In this system, the methane concentration upper threshold level for starting the flare is set at 20% methane gas to total gases. When the methane sensor detects a methane concentration of 20% or higher from the Input, a signal is sent from the Relay Port of the Main Controller to the Flare Control Board to start the flare. The methane concentration lower threshold level is set at 19% methane gas to total gases. When urethane gas concentration falls below 19% methane gas to total gases, a signal is sent from the Main Controller to the Flare Control Board to stop the flare from operating. The threshold concentration limits were determined by observations in the field of the minimum concentration of methane needed to maintain flare temperature above 1200° F. for maximum methane destruction.

It was observed that a concentration of 20% methane or higher ensured a consistent start-up for optimum temperature in the flare furnace of 1500° F. With a methane concentration of 20% or higher the flare would start and run for hours. If methane concentrations fell below 19% the flare temperature would fall below 1200° F. and the low concentration and low temperature shut-off signal would shut down the flare. Once installed, day for several days. When the methane concentration began to drop, the flare ran less often. As of May 2019, the flare only runs for 4 to 6 hours a day.

Figure 6:
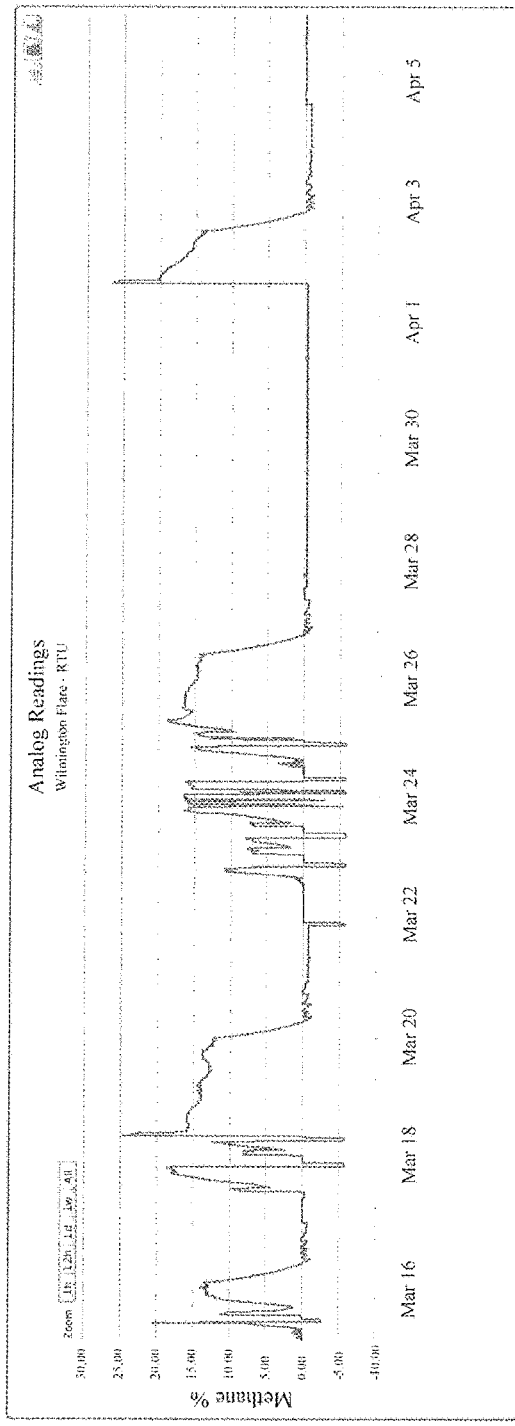
FIG. 6 shows select data from the Chandlers Recycling Ascon Landfill in Wilmington, Calif. test site, panel (A) shows methane concentration and panel (B) shows flare flow rates during the same period of time from about Mar. 15, 2019 to about Apr. 6, 2019.
Figure 6:
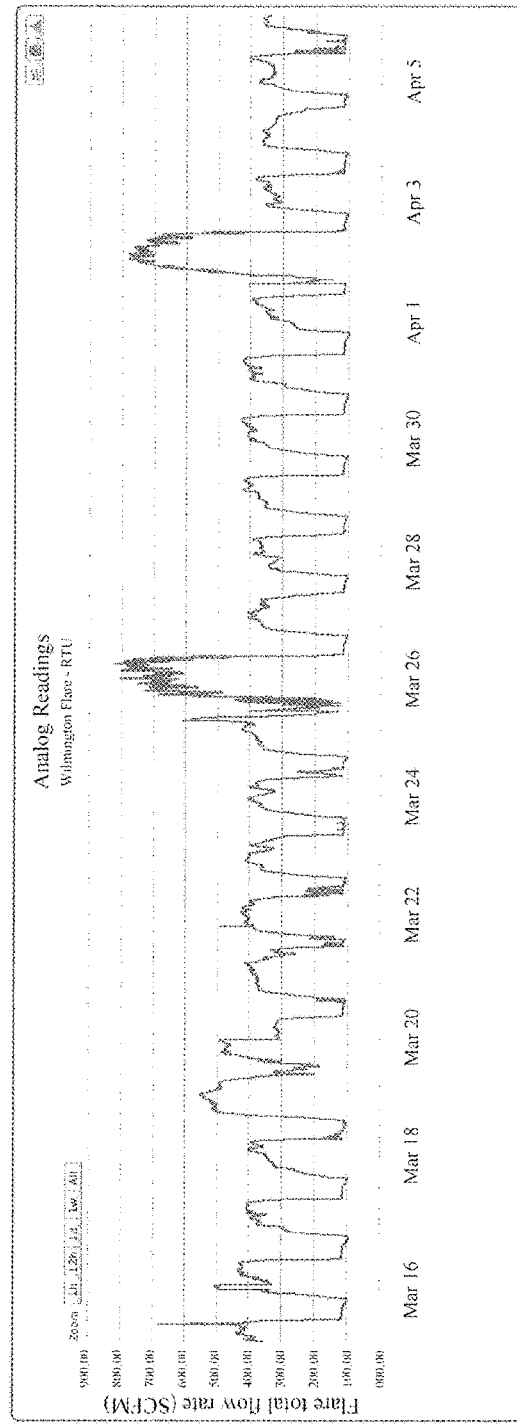

FIG. 6 shows two graphs depicting data from the Wilmington, Calif. test site. FIG. 6A is actual methane concentration (% vol.) remotely monitored from about Mar. 16, 2019 to about Apr. 5, 2019. FIG. 6B shows flare operation measured by flare total flow rate (SCFM) of wellhead ambient air over the same time period.

In FIG. 6A, the methane concentration measured by the remote sensor is represented graphically where the vertical axis of the graph (X) is the percent concentration of methane and the horizontal axis (Y) is the measurement time line in hours and days. In FIG. 6B, the run time of the flare is represented graphically where the vertical axis of the graph (X) is the flow rate displayed in standard cubic feet per minute and the horizontal axis (Y) is the time line measured in hours and days.

When viewing the two graphs in parallel time intervals, the two graphs clearly display the effect the methane concentration has on starting and stopping the flare system automatically. When the methane concentrations are at the "start" threshold the flare starts up. When the methane concentrations are at the "stop" threshold the flare shuts down. This represents the effectiveness of the RGMS system controlling the flare system to the optimum efficiency of methane concentration to run-time algorithm programmed into the system. There are several times when the flare was manually started but failed to operate due to low methane concentrations (March $21^{st}$ to March $23^{rd}$, and March $27^{th}$ to April $1^{st}$). As is shown, flare total flow rate was about 400 standard cubic feet per minute (SCFM) but a lack of methane concentration and low temperature caused the flare furnace to shut down. This demonstrates that even when manual override attempts are made to run the flare system with the sensing system on, the RGMS program still operates under the prescribed algorithm and shuts the flare system down when the proper "stop" threshold is reached.

The foregoing discussion and the examples are illustrative of the present invention, and should not be construed as limiting. The system can be designed to monitor a number of different gasses. The foregoing description focused on methane monitoring at landfill sites but in no way limits the application of the invention to solely monitoring of methane gas or solely to monitoring of landfill sites. Sensors are available for detection of a number of gasses or other known chemicals or compounds. Threshold monitoring levels for alerts and flare or other destruction system control can be adjusted based on the target compound being monitored. Still other variations within the spirit and scope of the claims are possible, and will readily present themselves to those skilled in the art.

What is claimed is:

1. A remote gas monitoring system consisting of:
a plurality of extraction wells connected in series with about 50-75% of the extraction wells equipped with wellhead sensors for monitoring soil-gas composition
each wellhead sensor having a power source, a timing system, a vacuum pump, a gas chamber, inlet and outlet lines, an infrared dual-gas sensor and sensor board, and a data acquisition and telecommunications system;
wherein the dual-gas sensor of each wellhead sensor measures the concentration of gasses drawn in by the vacuum pump and the measured concentrations are relayed to the data acquisition and telecommunications system and transmitted to a database system via a cellular communications network;
wherein said wellhead sensors continuously relay in real time soil-gas composition data to a computing system.

2. The monitoring system of claim 1 wherein each wellhead sensor is hard-wired to the computing system.

3. The monitoring system of claim 1 wherein each wellhead sensor is capable of wirelessly relaying soil-gas composition data to the computing system.

4. The remote gas monitoring system of claim 1 wherein the wellhead sensors monitor methane gas concentration.

5. The remote gas monitoring system of claim 4 wherein when one or more wellhead sensors detect a methane concentration exceeding a predetermined threshold level an alarm is energized.

6. The remote gas monitoring system of claim 1 wherein the power source of each wellhead sensor provides power to the timing system and the data acquisition and telecommunications system and the timing system provides power to the sensor board and the vacuum pump at periodic intervals, the vacuum pump draws gas vapors into gas chamber under vacuum from a surface or subsurface gaseous point, the dual-gas sensor is housed in the gas chamber and measures the concentration of gasses drawn in by the vacuum pump and through the sensor board the measurement data is relayed to the data acquisition and telecommunications system and is transmitted to a database system via a cellular communications network.

7. A remote gas monitoring system comprising:
a plurality of extraction wells connected in series with about 50-75% of the extraction wells equipped with wellhead sensors for monitoring soil-gas composition wherein said wellhead sensors continuously relay in real time soil-gas composition data to a computing system, said sensors monitoring the soil-gas composition for a concentration of a target landfill gas;
each wellhead sensor having a power source, a timing system, a vacuum pump, a gas chamber, inlet and outlet lines, an infrared dual-gas sensor and sensor board, and a data acquisition and telecommunications system;
wherein the dual-gas sensor of each wellhead sensor measures the concentration of gasses drawn in by the vacuum pump and the measured concentrations are relayed to the data acquisition and telecommunications system and transmitted to a database system via a cellular communications network;
said system including a piping network in confined flow communication with said plurality of extraction wells and having a common landfill gas supply conduit;
a landfill gas feed valve operably connected to the landfill gas supply conduit;
a flare furnace operably connected to the piping network and the common landfill gas conduit;
a temperature control thermocouple for monitoring flare furnace temperature;
a spark-ignited pilot operably associated with the flare furnace;
a pilot gas supply operably connected to the spark-ignited pilot; and
a controller in communication with the wellhead sensors, the landfill gas feed valve, the temperature control thermocouple, the spark-ignited pilot, the pilot gas supply, and the flare furnace;
wherein when the target landfill gas concentration exceeds a predetermined upper threshold level at a minimum of about 5 percent of the wellhead sensors:
the controller signals the pilot gas supply and the spark-ignited pilot to ignite the flare furnace and the thermocouple monitors the flare furnace temperature;
wherein when the flare furnace temperature reaches a predetermined minimum temperature, the controller signals the landfill gas feed valve to open, supplying landfill gas from said landfill gas conduit to said flare furnace; and
wherein when the target landfill gas concentration at no more than 3 percent of the wellhead sensors exceeds a predetermined lower threshold level:
the controller signals the landfill gas feed valve to close; and
the controller signals the flare furnace to shut down.

8. The remote gas monitoring system of claim 7 wherein the power source of each wellhead sensor provides power to the timing system and the data acquisition and telecommunications system and the timing system provides power to the sensor board and the vacuum pump at periodic intervals, the vacuum pump draws gas vapors into gas chamber under vacuum from a surface or subsurface gaseous point, the dual-gas sensor is housed in the gas chamber and measures the concentration of gasses drawn in by the vacuum pump and through the sensor board the measurement data is relayed to the data acquisition and telecommunications system and is transmitted to a database system via a cellular communications network.

* * * * *